United States Patent [19]

Preda et al.

[11] Patent Number: 5,147,805
[45] Date of Patent: Sep. 15, 1992

[54] METHOD AND KIT FOR DETERMINING THE FUNCTIONAL ACTIVITY OF PROTEIN S IN HUMAN PLASMA

[75] Inventors: Luigi Preda, Verano Brianza; Antonio Lombardi, Cinisello Balsamo, both of Italy

[73] Assignee: Instrumentation Laboratory S.r.l., Milan, Italy

[21] Appl. No.: 548,224

[22] Filed: Jun. 29, 1990

[30] Foreign Application Priority Data

Jul. 7, 1989 [IT] Italy .................. 21128 A/89

[51] Int. Cl.$^5$ .................. G01N 33/68; G01N 33/86
[52] U.S. Cl. .................. 436/86; 436/69; 436/517; 435/7.2; 435/13; 435/7.91; 435/291; 435/975; 422/61; 422/73
[58] Field of Search .................. 435/13, 7, 7.2, 7.91, 435/291, 975; 436/517, 518, 69, 86; 422/73, 61

[56] References Cited

U.S. PATENT DOCUMENTS 4,849,340  7/1989  Oberhardt .................. 435/13

FOREIGN PATENT DOCUMENTS 2571497  4/1986  France .
89/00205  1/1989  PCT Int'l Appl. .

OTHER PUBLICATIONS

Joist, J. H. "Tests of Blood Coagulation", Granwohl's Clinical Laboratory Methods and Diagnosis, Ed. ALex C. Sonnawirth et al. 8th ed. vol. 1, St. louis: C. V. Mosby Co., 1980 1013-1039. 2 vol.
T. Kamiya et al., "Inherited Deficiency of Protein S . . . " Blood, vol. 62(2) pp. 406-410 (Feb. 1986).
A. D'Angelo et al., "Acquired Deficiencies of Protein S" J. Clin. Invest. vol. 81, pp. 1445-1454 (May 1988).
P. Comp et al., "Familial Protein S Deficiency Is Asso-
ciated ... " J. Clin. Invest vol. 74, pp. 2082-2088 (Dec. 1984).
K. Suzuki et al., "Plasma Protein S Activity Measured using PROTAC . . . ", Thrombosis Research 49: pp. 241-251 (1988).
R. Peters et al., Biological Abstracts 88 (6) 58010 (1989).
B. P. Van de Waart, "A Functional Test for Protein S Activity In Plasma", Thrombosis Research 48: pp. 427-437 (1987).
F. J. Walker, "Protein J. and The Regulation Of Activated Protein C", Seminars In Thrombosis & Hemostasis, vol. 10, No. 2, pp. 131-138 1984.
C. A. Fulcher et al., "Proteolytic Inactivation of Human Factor VIII . . . ", Blood, vol. 63, No. 2, pp. 486-489 (Feb. 1984).
L. Preda et al., "A Prothrombin Time-Based Functional Assay of Protein S", Thrombosis Research, vol. 60, pp. 19-32 (1990).
Susuki, K. et al. "Plasma protein S activity measured using Protac, a snake venom derived activator of protein C." Thromb. Res. 49/2 (241-251) 1988.

*Primary Examiner*—James C. Housel
*Assistant Examiner*—David Redding
*Attorney, Agent, or Firm*—Pennie & Edmonds

[57] ABSTRACT

To determine the biological activity of protein S in a sample of human plasma, the suitably diluted sample is added to a substrate formed from plasma deficient in protein S, in which protein C is activated. The functionality of protein S is evaluated by a coagulometric test using bovine thromboplastin with added calcium as the phospholipid source. Also disclosed is a kit for determining the activity of Protein S in a human plasma sample. The kit includes a first reagent which is human plasma deficient in protein S, a second reagent which contains an activator for protein C, and a third reagent which contains bovine thromboplastin.

14 Claims, 1 Drawing Sheet

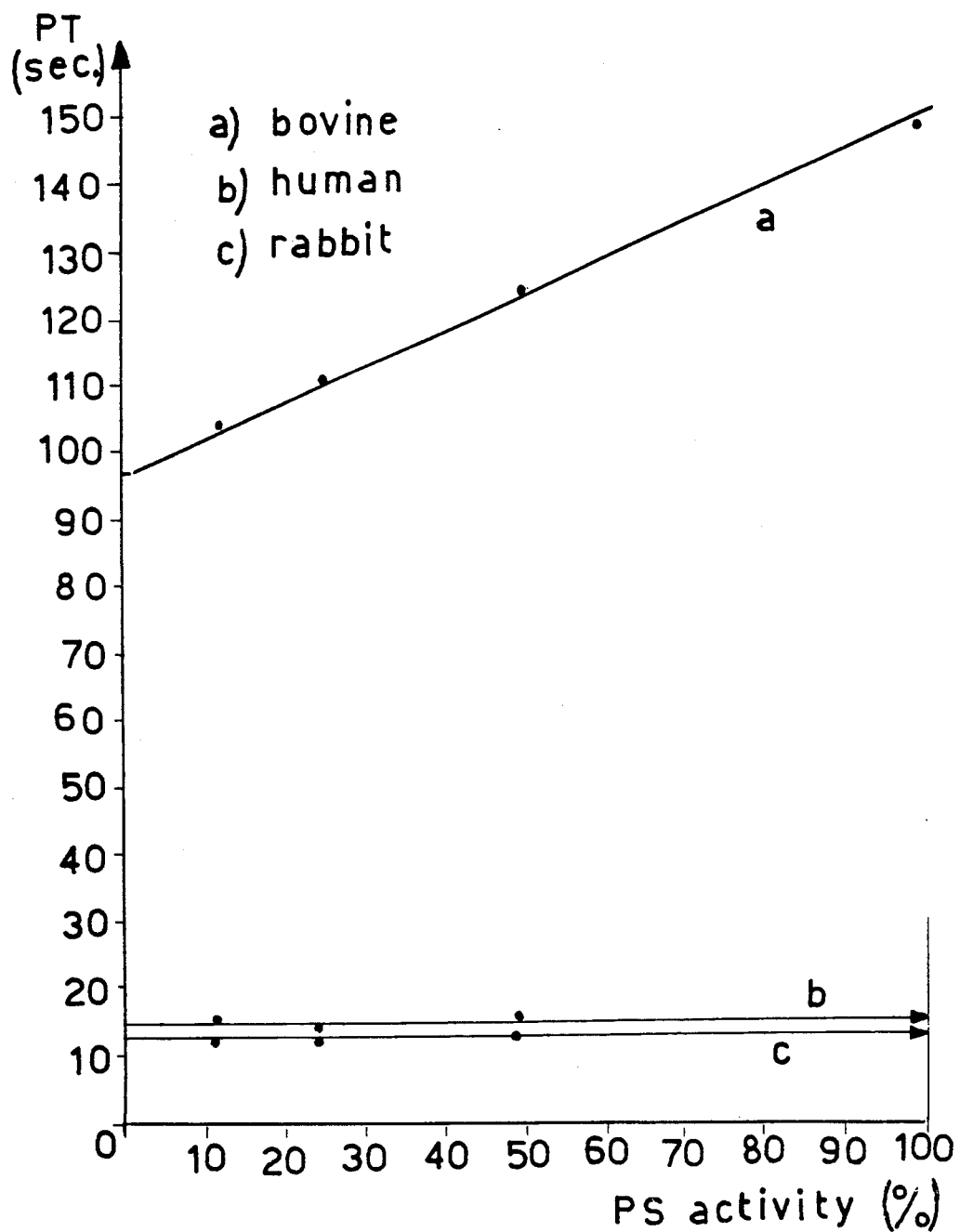

5,147,805

METHOD AND KIT FOR DETERMINING THE FUNCTIONAL ACTIVITY OF PROTEIN S IN HUMAN PLASMA

BACKGROUND OF THE INVENTION

Protein S is a vitamin K-dependent plasmatic protein known since 1977. Initially, no function was attributed to protein S and only recently has its role in manifesting the anticoagulant activity of activated protein C been proposed.

Protein C is a protein of the prothrombinic complex the function of which is to inhibit the enzymatic cascade of plasmatic coagulation at Factor V and Factor VIII level.

Clinical studies have also shown that patients congenitally deficient in protein C are prone to frequent thrombosis. In vitro studies have shown that protein S acts as cofactor for activated protein C. These studies have therefore suggested that protein S is essential for manifesting the anticoagulant effects of activated protein C.

As protein S is necessary for the optimum expression of the anticoagulant activity of activated protein C, it has been suggested that a deficiency of protein S can make an individual prone to illnesses of a thrombotic nature.

The determination of protein S.in the plasma is therefore of great interest, in that its greater or lesser deficiency constitutes a thrombosis risk factor.

In human plasma, protein S forms a equimolar complex with another plasmatic protein, namely C4b-BP.

At equilibrium under physiological conditions protein S exists in two forms, namely protein S bound to C4b-BP (=60%) and free protein S. Free protein S is the only form to exhibit the biological function of cofactor for activated protein C.

The methods proposed up to now for determining the biological activity of protein S basically comprise this series of steps:

mixing the sampLe to be tested, either w or suitably diluted, with plasma deficient in protein S;

adding an optimum quantity of activated protein C or PROTAC, to activate the protein C of the deficient plasma;

adding an optimum quantity of phospholipids and, if it is necessary, of activated factor;

adding $CaCl_2$ as initiator for the coagulation reaction;

evaluating the activity of protein S in the sample by expressing it as a percentage calculated from a calibration curve which has been constructed using a plasma pool from healthy individuals, for which the protein S activity is assigned the value 100%.

Functional tests for measuring the activity of protein S in plasma are described for example in "Thrombosis Research" vol. 48, 427–437, 1987 (P. van de Waart et al.) and idem vol. 49, 241-251, 1988 (K. Suzuki et al.); in "Blood" vol. 67, 406–410, 1986 and in "J. Clin. Invest." vol. 81, 1445-1454, 1988 and vol. 74, 2082-2086, 1984.

These tests are therefore based on the capacity of protein S to serve as cofactor for the anticoagulant effects of activated protein C. The prolongation of the coagulation time induced by activated protein C depends on the content of protein S in the plasma of the sample.

The object of the invention is to provide a method for determining the functional activity of protein S which can be carried out using not excessively complicated techniques in normal analysis laboratories at acceptable cost, and with greater accuracy and repeatability than with the previously proposed methods.

SUMMARY OF THE INVENTION

To this end, according to the invention, the method for determining the activity of protein S in a human plasma sample comprises adding the plasma sample to activated substrate plasma, and measuring a parameter related to the time within which the coagulation reaction occurs.

State differently, the present invention provides a method for determining the activity of prote in a human plasma sample comprising combining the plasma sample with activated substrate plasma, then combining the mixture with bovine thromboplastin to initiate a coagulation reaction and measuring a parameter related to the time within which the coagulation reaction occurs.

The present invention also provides a kit for determining the activity of protein S in a human plasma sample which comprises:

a) a first reagent which is human plasma deficient in protein S, b) a second reagent which contains an activator for protein C, and c) a third reagent which contains bovine thromboplastin.

BRIEF DESCRIPTION OF THE DRAWING

The Figure is a graph illustrating a protein S test wherein the relationship of prothrombin time to the percentage of protein S is indicated. The percentage of protein S indicated in the Figure as "PS(%)" is based upon a pooled plasma for healthy individuals having a 100 percent protein S content.

DETAILED DESCRIPTION OF THE INVENTION

To better clarify the basic principles of the present invention, a description is given hereinafter by way of example of its possible implementation in determining the activity of protein S in human plasma.

In the determination method according to the invention the plasma deficient in protein S with which, after activation, the sample to be tested is mixed, can be obtained by any of the various known techniques, the only limitation being that the activity of the free protein S must be less than 1%.

Thus, in this description plasma deficient in protein S means a plasma with a very low level of free protein S activity, preferably less than 1%, commonly obtained by immunoadsorption methods using anti-protein S antibodies (mono or polyclonal). To prepare the activated substrate plasma for use in the method according to the invention, the plasma deficient in protein S is mixed with a protein C activator, which can be any substance able to satisfy this function; PROTAC, ie one or more purified fractions of Agkistodon contortrix venom, for example has proved particularly suitable and simple.

The activation can also be conducted in the heterogeneous phase by adding the deficient plasma to be activated to an inert support to which the activator is bound. The activator can be one or more purified fractions of Agkistodon contortrix venom, or human or bovine thrombin.

In the described example of implementation of the method according to the invention, the PROTAC was used (1.5 U/ml) in the proportion on 1 part per 2 parts of protein S-deficient plasma.

The mixture of protein S-deficient plasma and PROTAC (representing the activated substrate plasma) should preferably be used about 15 minutes after its preparation, when the activation value has reached a high level.

It should also preferably be used within 60 minutes, this time period being that within which the decrease in the level of activation of the protein C is negligible, this decrease being due to the presence in the protein S-deficient plasma of the physiological inhibitor of activated protein C.

To carry out the determinations in accordance with the method of the invention it is firstly necessary to construct the calibration curve with which to compare the results of the human plasma sample analyzes.

For this purpose, standards are prepared by forming mixtures with pooled plasma from healthy individuals and protein S-deficient plasma, this latter varying from 0 to 100% of the two components. Each standard is diluted 1:10 and a 100 mM NaCl solution, the diluted standard being added to the activated substrate plasma in the ratio 1:1.

Bovine thromboplastin with added calcium is then added to the mixture of the standard in activated substrate plasma in such a quantity as to cause this mixture to coagulate in a time of not less than 60 seconds. The thromboplastin used is in the form of an aqueous suspension of tissue extract, as usual.

For example, the quantities of the various reagents used in the test can be as follows:

| | |
|---|---|
| Activated substrate plasma | 40 ul |
| Sample (ie standard) | 40 ul |
| Bovine thromboplastin | 80 ul |

The prothrombin time (a common coagulation measurement, known as PT, which is preferably performed in a cuvette of a rotor in the apparatus described in U.S. Pat. No. 4,777,141 to Calzi et. al., Oct. 11, 1988) is then measured for each standard, to obtain the calibration curve.

In the determination method according to the invention, the plasma samples to be tested are subjected to a procedure identical to that described for the standards and with identical dilution. The protein S activity is evaluated by comparing the results obtained with a calibration curve.

As described above, the kit of the present invention comprises a first reagent, a second reagent and a third reagent. The activator for protein C in the second reagent is preferably a purified fraction of Agkistodon contortrix venom, such as the PROTAC product described above. The third reagent preferably contains, in addition to bovine thromboplastin, calcium ions and phospholipids.

It should be noted that the use of bovine thromboplastin with added calcium as proposed by the invention results in an analysis method which is surprisingly sensitive compared with the use of thromboplastin of other origin, such as human or rabbit. In this respect, the PT variations obtained using bovine thromboplastin with added calcium, when measured for example between the PTs obtained with the end 0% and 100% standards, are approximately 50 seconds. Using thromboplastin of other origin, the corresponding PT variations are only a fraction of this time, for example just a few seconds.

The greater sensitivity and repeatability of the method of the invention are therefore apparent when bovine thromboplastin with added calcium is used. This sensitivity can be immediately evaluated from the accompanying figure, which shows graphically the behaviour of the different thromboplastins. On the graph of the figure the vertical axis represents the PT values obtained for different standards, which are indicated on the horizontal axis with values from 0 to 100, representing their percentage content of pooled plasma from healthy individuals. Curve a) shows the values obtained using bovine thromboplastin in the method of the invention, whereas curves b) and c) show values obtained by the same procedure, but using human and rabbit thromboplastin respectively.

The previously described exemplary procedures for conducting the method according to the invention indicate those concentration values and mixing ratios which have been found advantageous in obtaining significant analytical results. These values must not however be considered critical and can be varied proportionally according to the requirements of the operator, without departing from the scope of the invention.

In the same manner, various current techniques can be used in carrying out the various specific steps in the method of the invention, and in particular for preparing starting substances, for preparing mixtures, for measuring the PT and for its display by means of a calibration curve. The calibration curve should demonstrate a significant variation of PT times as a function of protein S concentration in order to provide meaningful results with samples to be analyzed.

In experiments based upon the above exemplary procedures the relationship between prolongation of PT time and protein S activity was substantially linear.

We claim:

1. A method for determining the activity of protein S in a human plasma sample comprising combining the plasma sample with activated substrate plasma to form a mixture, then combining the mixture with bovine thromboplastin in the presence of calcium ions to initiate a coagulation reaction and measuring a parameter related to the time within which the coagulation reaction occurs.

2. A method as claimed in claim 1 wherein the bovine thromboplastin is provided as an initiating reagent also containing phospholipids.

3. A method as claimed in claim 1, wherein the parameter related to the time within which the coagulation reaction occurs is the prothrombin time (PT).

4. A method as claimed in claim 3 wherein the PT value measured for a sample to be tested is compared with PT values obtained for pooled plasma from healthy individuals.

5. A method as claimed in claim 1 wherein the activated substrate plasma with which the sample is admixed has been formed from a mixture of plasma deficient in protein S with a protein C activator.

6. A method as claimed in claim 5 wherein the protein C activator is at least one purified fraction of Agkistodon contortrix venom.

7. A method as claimed in claim 1 wherein the activated substrate plasma with which the sample is admixed has been formed by contacting a plasma deficient in protein S with a protein C activator bound to an insoluble medium.

8. A method as claimed in claim 7 wherein the protein C activator is at least one purified fraction of Agkistodon contortrix venom.

9. A method as claimed in claim 1 wherein the activated substrate plasma with which the sample is admixed has been formed by contacting a plasma deficient in protein S with thrombin bound to an insoluble medium.

10. A method as claimed in claim 1 wherein the activated substrate plasma has been prepared by activating the protein C in a protein S deficient plasma and then performing the admixing and combining steps sufficiently quickly for the protein C activity to be high at the time that the coagulation reaction is initiated.

11. The method of claim 10 wherein the coagulation reaction is initiated 15 to 60 minutes after the protein C is activated in the protein S deficient plasma.

12. A kit for determining the activity of protein S in a human plasma sample which comprises:
   a) a first reagent whcih is human plasma deficient in protein S,
   b) a second reagent which contains an activator for protein C, and
   c) a third reagent which contains bovine thromboplastin and calcium ions.

13. The kit of claim 12 wherein the second reagent contains a purified fractin of Agkistodon contortrix venom.

14. The kit of claim 12 wherein the third reagent further contains phospholipids.

* * * * *